United States Patent
Laghi et al.

(10) Patent No.: US 8,349,021 B2
(45) Date of Patent: *Jan. 8, 2013

(54) PROSTHETIC LOCKING LINER WITH IMPROVED KNEE FLEXION

(75) Inventors: Aldo A. Laghi, Clearwater, FL (US); Kevin McLoone, Dunedin, FL (US)

(73) Assignee: ALPS Intellectual Property Management, LLC, St. Petersburg, FL (US)

( * ) Notice: Subject to any disclaimer, the term of this patent is extended or adjusted under 35 U.S.C. 154(b) by 36 days.

This patent is subject to a terminal disclaimer.

(21) Appl. No.: 13/159,549

(22) Filed: Jun. 14, 2011

(65) Prior Publication Data

US 2011/0270414 A1    Nov. 3, 2011

Related U.S. Application Data

(63) Continuation-in-part of application No. 12/454,299, filed on May 14, 2009, now Pat. No. 8,226,732.

(60) Provisional application No. 61/053,036, filed on May 14, 2008.

(51) Int. Cl.
*A61F 2/80* (2006.01)

(52) U.S. Cl. ........................................................ 623/36

(58) Field of Classification Search ............... 623/33–37, 623/57–59
See application file for complete search history.

(56) References Cited

U.S. PATENT DOCUMENTS

| | | | |
|---|---|---|---|
| 4,479,272 A | 10/1984 | Beldzisky | |
| 5,603,122 A | 2/1997 | Kania | |
| 6,454,812 B1 | 9/2002 | Laghi | |
| 7,169,122 B2 | 1/2007 | Gros-Jean et al. | |
| 8,226,732 B2 * | 7/2012 | Laghi et al. | 623/36 |
| 8,246,694 B2 * | 8/2012 | Laghi et al. | 623/36 |
| 2003/0060845 A1 | 3/2003 | Gardon-Mollard | |
| 2005/0101693 A1 | 5/2005 | Arbogast et al. | |
| 2005/0149202 A1 | 7/2005 | Schaeffer et al. | |
| 2010/0016993 A1 | 1/2010 | Mackenzie | |
| 2010/0274363 A1 | 10/2010 | Laghi et al. | |
| 2011/0208321 A1 * | 8/2011 | Doddroe et al. | 623/36 |

* cited by examiner

*Primary Examiner* — Bruce E Snow
(74) *Attorney, Agent, or Firm* — Henry J. Recla (57) ABSTRACT

A prosthesis comprising an elastomeric locking liner sized and configured to surround a limb of a patient about a knee joint, the liner having an inner surface for facing the limb of the patient and an outer surface defining an anterior region and a posterior region which are demarcated by an imaginary plane extending midway between the front most portion and rear most portion of the limb along the length of the limb, wherein the anterior region has an anterior material secured thereto and the posterior region has a posterior material secured thereto and the anterior and posterior materials having equal transverse elongation, and the anterior material having a longitudinal elongation greater than the longitudinal elongation of said posterior material, whereby when said prosthesis is donned onto a limb of a patient over the knee and the limb is flexed about the knee, buckling of the prosthesis about the knee is substantially reduced or eliminated and wherein the distal end of the liner includes an insert member adapted to receive a connector for locking the liner to a prosthetic socket when worn on a residual limb of an amputee.

21 Claims, 7 Drawing Sheets

PROSTHETIC LOCKING LINER WITH IMPROVED KNEE FLEXION

This application is a continuation-in-part of U.S. Nonprovisional application Ser. No. 12/454,299 filed on May 14, 2009, now U.S. Pat. No. 8,226,732 which claims priority to U.S. Provisional Application No. 61/053,036 filed on May 14, 2008, hereby incorporated by reference. This application is related to application Ser. No. 12/832,653 filed on Jul. 10, 2010.

BACKGROUND

A challenging aspect of treating those who have lost one or more limbs is the restoration of function to the remaining limb (residual limb). Such a restoration often means fitting the residual limb with one or more prostheses, or artificial limbs. A difficulty with artificial limbs is that they often do not physically interface well with the amputee. For instance, most prostheses comprise a cup into which the residual limb, protected with an elastomeric sheath or "liner," is inserted and secured. Since the 1980's, prosthetic liners have generally been of polymeric materials. Such liners are described in U.S. Pat. Nos. 5,549,709; 6,645,253; 6,761,742; 6,554,868; 6,726,726; 6,926,742 and 6,974,484.

Current liner designs available to amputees are generally simple. Many are based upon a single-layer elastomeric sleeve, usually with a slight taper from the open end to a blunted closed end. Because of such simplicity of design, the liners can be manufactured in large numbers from easily worked materials at a relatively low cost and without the need for extra steps or machinery.

However, amputees who have been fortunate enough to retain limb joints, such as knee or elbow joints, can find the relatively simple design of commonly available elastomeric liners to be inadequate. For example, amputees having below-the-knee prosthetics generally require a liner having the ability to conform to a range of conformations accessed by an intact, functioning knee joint. A problem with many commercially available liners is that their simple construction and design, largely dictated by ease and relatively low costs of manufacture, generally fails to conformationally accommodate the knee joint as it undergoes a full range of motion. Simple sleeve-type liners often do not provide a comfortable fit over the entire range of motion of the joint. Even at small bending angles, the fit of the liner behind the knee can be lost due to bunching or gathering behind the knee ("buckling"). Buckling is the development, upon flexion of the knee joint, of one or more folds in the portion of the liner overlying the region behind the knee (popliteal fossa). The folds generally occur in a lateral direction, i.e., roughly perpendicular to the length of the leg. However, more complex, crinkle-type folds can also occur. The pinching and pulling of underlying skin which can occur with buckling can result in patient discomfort. Moreover, many liner-wearers also experience sweating behind the knee, which can exacerbate the discomfort caused by buckling.

As the knee joint undergoes flexion, the relatively relaxed liner surface disposed over the kneecap (the "anterior surface") must stretch and bend in order to accommodate the change in conformation of the knee joint, as well as the increase in anterior skin surface area which accompanies the change. The maximum stretch occurs when the knee joint is at its fully bent position. The liner surface behind the knee (the "posterior surface") must also accommodate changes in the conformation of the joint during bending. However, unlike the anterior surface, it must accommodate a reduction in the vertical dimension as it takes on a bent conformation. Upon joint flexion, while the anterior surface can easily stretch and still smoothly overlay the skin, the posterior surface is essentially required to assume a "contracted" conformation in order to continue to smoothly overlay the area behind to the knee.

When elastomeric liners flex with the knee, the liner portion disposed over the knee cap (the "anterior portion") stretches in the longitudinal direction (i.e., along the length of the leg, and contracts to a degree in the transverse direction (i.e., across the front of the leg, and in a direction generally perpendicular to the longitudinal direction). In order to maintain a buckle-free fit, the liner portion overlying the area behind the knee (the "posterior portion") preferably will stretch in the transverse direction and contract in the longitudinal direction. The transverse contraction of the anterior portion will aid in stretching the posterior region transversely to a degree, which, in turn, will cause the anterior region to contract longitudinally to a degree.

It should be noted that substantially thickening the posterior region can have the affect of simultaneously reducing buckling and impeding the aforementioned contraction. However, such a solution is generally not conducive to wearer comfort in that it can increase the stiffness of the liner and impede its ability to undergo the angular bend required by flexion.

Current polymeric/elastomeric gel liner materials having the suppleness necessary for wearer comfort generally easily accommodate the anterior stretching, but posteriorly, such materials can be prone to buckle upon flexion. Efforts to eliminate buckling by fabricating liners from materials having increased "stiffness," such as by using materials having low elongation, tend to reduce the ability of the liner overlying the anterior portion of the knee to stretch and accommodate flexion of the knee joint, leading to increased wearer discomfort. Furthermore, the fabrication of a liner having anterior characteristics different from posterior characteristics, such as, for example, a continuous but non-homogeneous liner, or a liner fabricated by edge-joining two or more different elastomeric surfaces is generally a poor solution in that it can be costly, and require a seam between the elastomeric regions with differing characteristics. Such a seam in a monolayer liner can be a zone of weakness and undesirable from the standpoint of liner integrity.

The use of material overlays in the posterior region to "stiffen" the liner by appreciably increasing the overall thickness of the liner overlying the posterior region can interfere with the ability of the posterior region to responsively conform during flexion of the knee joint. Wearer discomfort is generally increased.

Thus, there is a need to produce comfortable liners which easily accommodate the wide range of motion of the knee joint without unnecessary posterior or anterior stiffness, and exhibit reduced or no buckling behind the knee upon flexion.

BRIEF SUMMARY OF THE INVENTION

Referring to the figures, the present invention solves the problem of buckling which can be reduced or eliminated by overlaying all or a portion of the part of the liner (L) intended to cover the anterior portion of the leg, wherein the overlay includes the forwardmost point of the patella (1), with a first material (2); overlaying all or a portion of the part of the liner intended to cover the posterior portion of the leg, wherein the overlay includes the popliteal fossa (3), with a second material (4); and laterally connecting the two overlays such that the first and second materials are elastically connected by a means (5) in addition to being attached to the underlying liner (L). The means (5) can be any conventional connection such as a strip of material attached along the edges of materials (2) and (4), or can be an overlap of one material edge adhered over the edge of the other as illustrated in FIG. 1A, or can be abutting edges sewn together with cross-stitches as illustrated in FIG. 1B.

In the preferred embodiments, the posterior portion of the elastomeric liner (L) is overlaid with a material (4) having a longitudinal and transverse modulus of elasticity (ME) greater than that of the elastomeric liner (L); the anterior portion of the elastomeric liner is overlaid with a material (2) having 1) a longitudinal and transverse ME greater than the ME of the elastomeric liner (L), and 2) a longitudinal ME which is greater than the longitudinal ME of the material (4) overlaying the posterior region. In other words, the liner (L) is easier to stretch in both the longitudinal and transverse directions than both materials (2) and (4), while the anterior material (2) is easier to stretch in the longitudinal direction than the posterior material (4).

Figure 2:
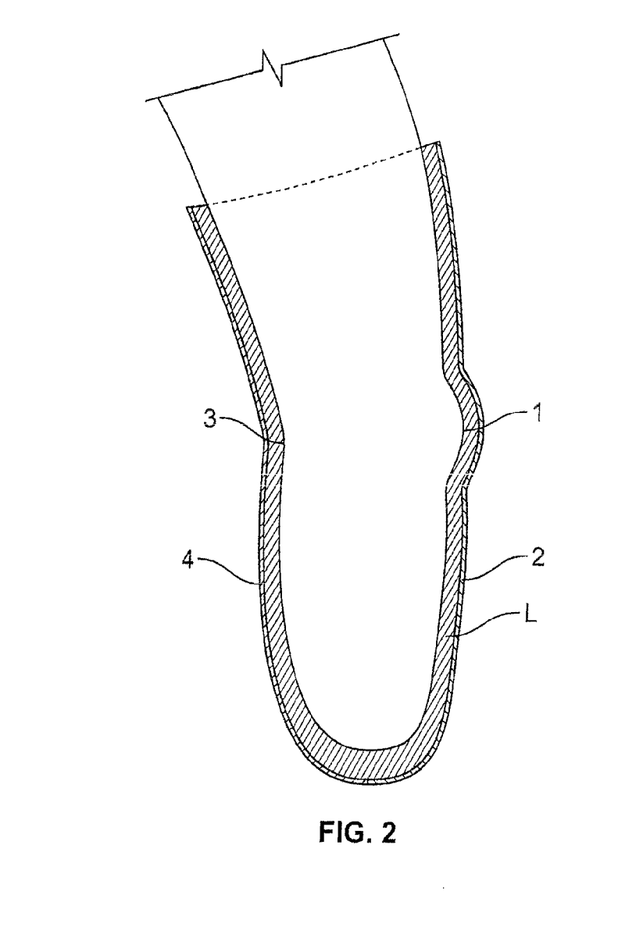
FIG. 2 illustrates a cross-sectional view of the liner of the present invention in an un-flexed position.

The term "popliteal fossa," a well-known anatomical term, is used according to its meaning in the art, to refer to the region behind the knee containing the "bend" when the knee joint is flexed. The popliteal fossa is generally the portion of the bend which is directly posterior to the knee joint (FIG. 2; 3). In the preferred embodiments, the posterior overlay comprises the entire "knee-bend" crease.

In the present invention, buckling is prevented by using an elastic fabric as the posterior material overlay, the anterior material overlay, or both. Moreover, even if the fabric has longitudinal and transverse elasticity which are partially or wholly independent of one another, reduced buckling is still observed. By "partially or wholly independent," it is meant that fabric stretched in the longitudinal direction causes little, if any, measurable contraction in the transverse direction. Preferred fabrics are knit fabrics made from stretchable yarns, which can have equal or different longitudinal or transverse elongations, as well as directional elasticities which are independent, or with some degree of dependence, as described above.

The reduction or elimination of buckling in the present invention can generally be observed by the fact that the materials are only present on the liner as a superficial covering, such as a fabric adhered thereto. The absence or reduction in buckling in general is due to the strategic placement and interconnection of the material overlays.

In particular, when the liner is overlaid with two elastic or elastomeric materials, such as, for example, elastic or elastomeric fabrics, or elastomeric polymeric materials; and wherein:
1) a first material having a high longitudinal elongation is adhered to the liner overlying the anterior region comprising the point of the liner directly anterior to the forwardmost point of the patella;
2) a second material having a low longitudinal elongation is adhered to the liner overlying the posterior region comprising the point of the liner directly posterior the popliteal fossa; and
3) the first and second materials are coupled to each other, directly or indirectly, on both sides of the knee, along the edges thereof that intersect a plane generally passing through the longitudinal extent of the residual limb generally midway between the anterior and posterior regions;

the liner generally exhibits reduced buckling behind the knee upon flexion, and, in many cases, exhibits no buckling and remains smoothly and continuously in contact with the wearer's skin.

DETAILED DESCRIPTION OF THE INVENTION

Figure 1:
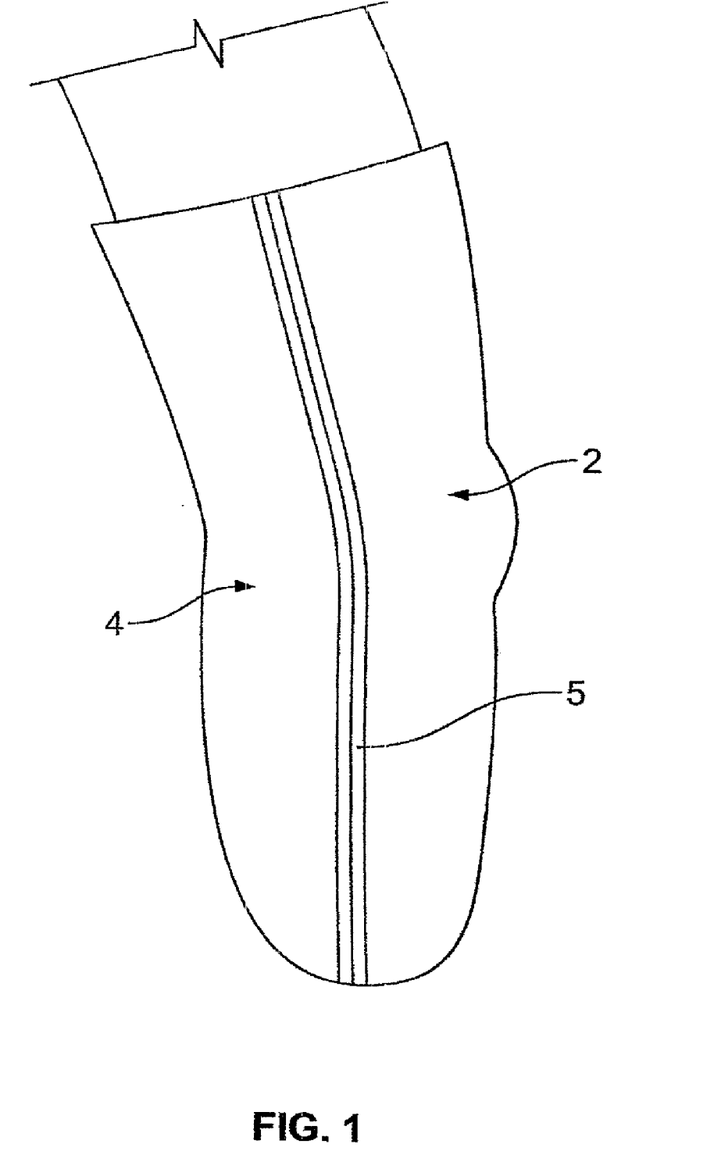
FIG. 1 illustrates a perspective view of the liner of a first embodiment of the present invention as a liner with anterior and posterior overlays.
Figure 1A:
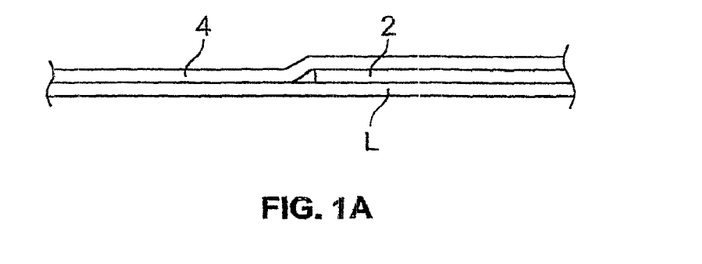
FIG. 1A illustrates an alternative embodiment of the present invention in which the edges of the anterior and posterior regions are connected together in an overlapping arrangement.
Figure 1B:
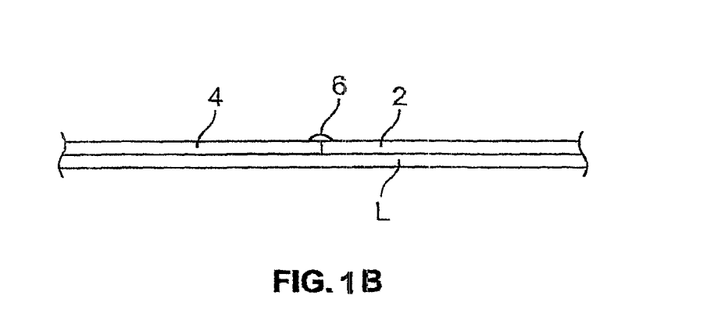
FIG. 1B illustrates an alternative embodiment of the present invention in which the edges of the anterior and posterior regions are connected together in an abutting arrangement.
Figure 3:
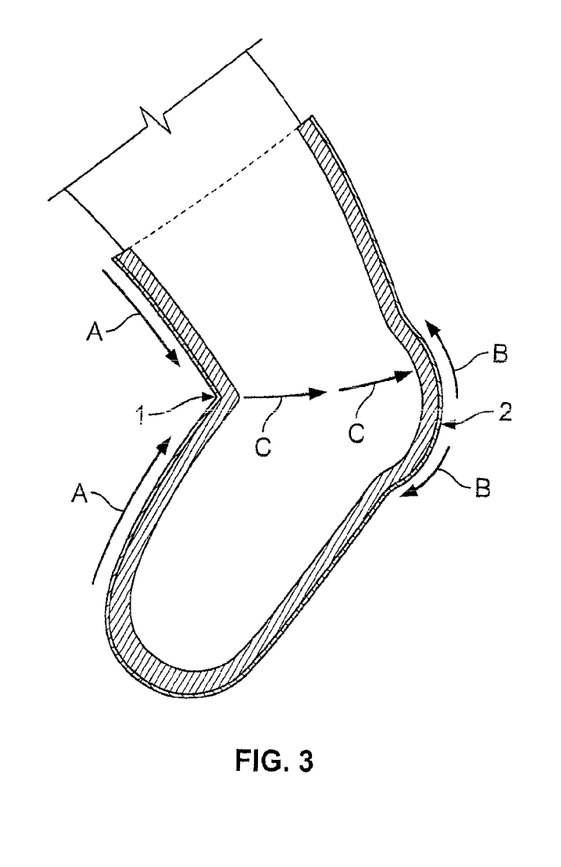
FIG. 3 illustrates a cross-sectional view of the liner of the present invention in a flexed position as indicated by arrows A, B & C.
Figure 4:
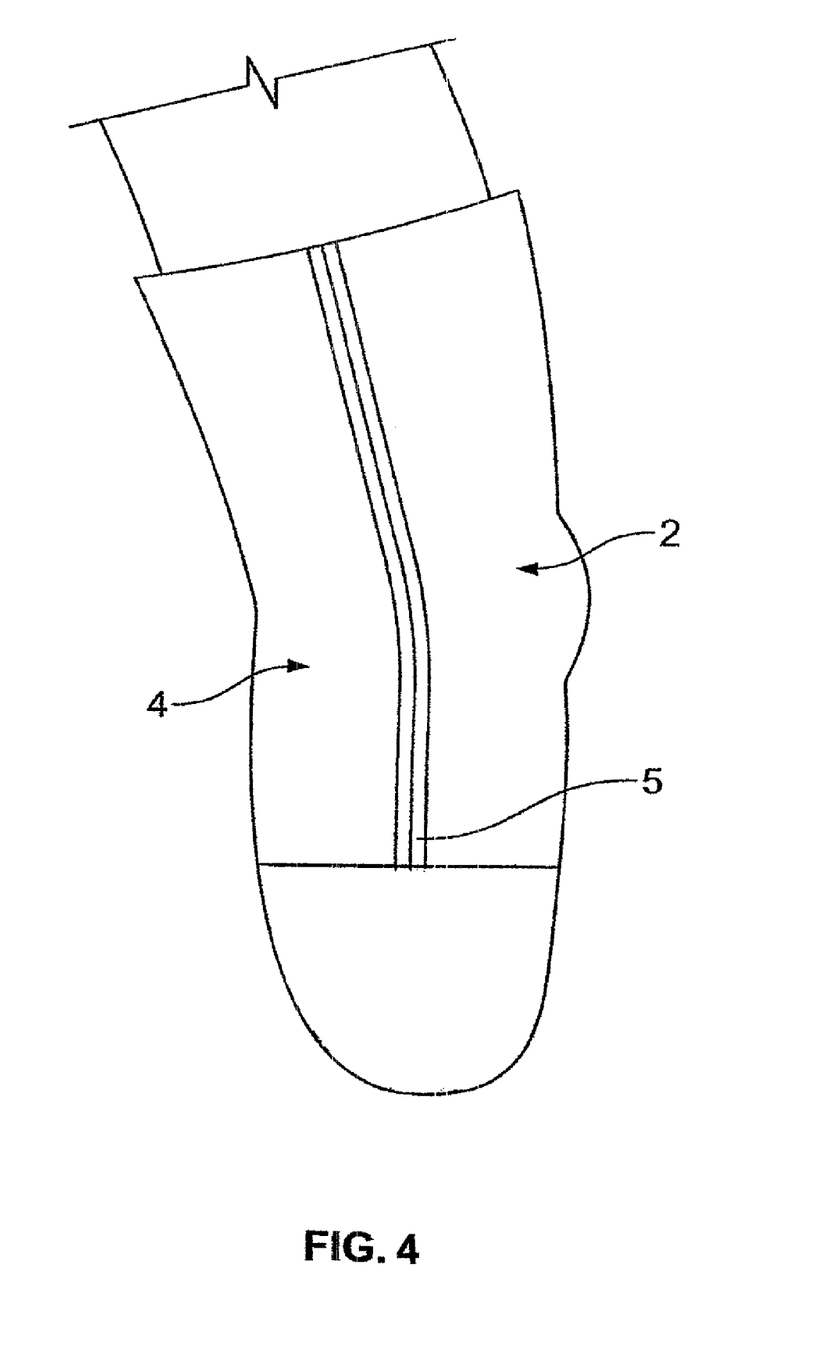
FIG. 4 illustrates an embodiment of the present invention in which the anterior and posterior overlays do not extend to the stump end of the liner, and are laterally connected by a seam.
Figure 5:
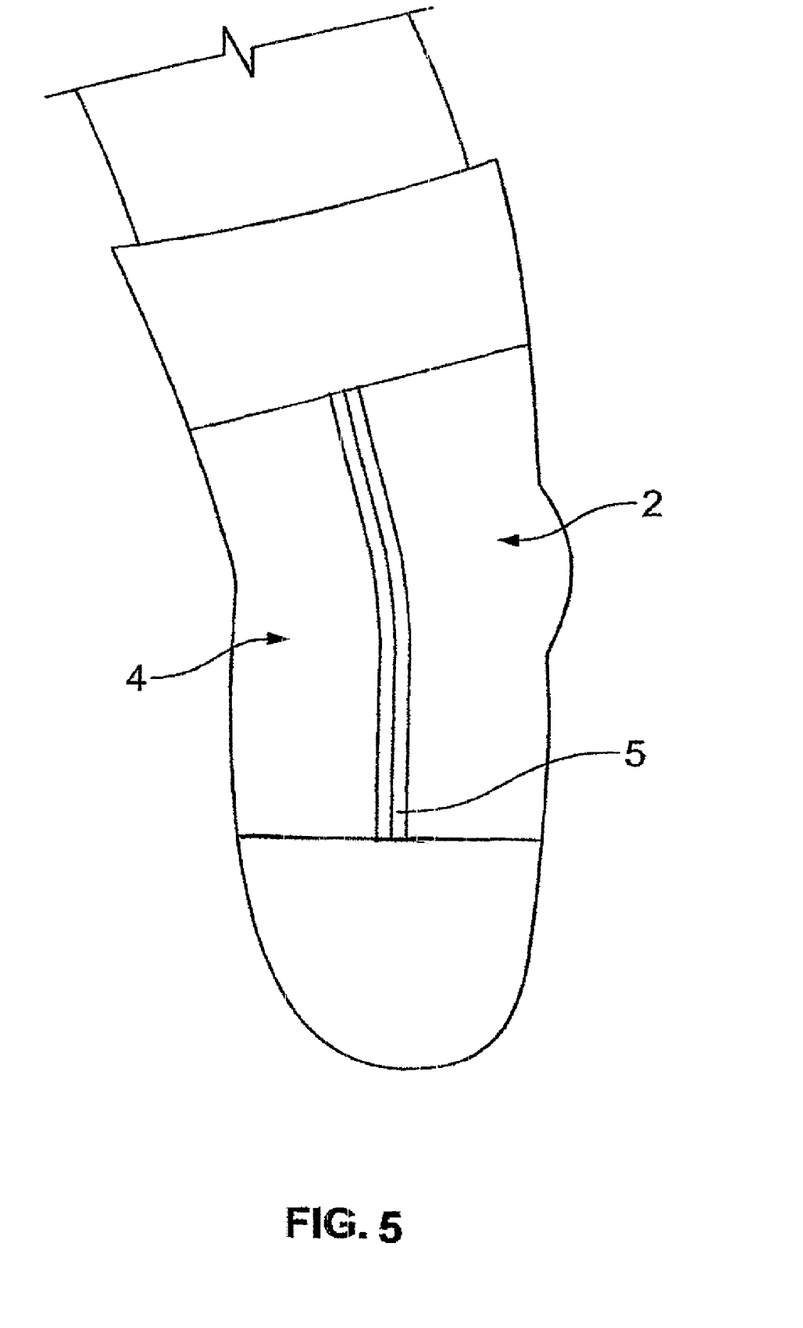
FIG. 5 illustrates an embodiment of the present invention in which the anterior and posterior overlays do not extend to the stump end or the open end of the liner, and are laterally connected by a seam.

Referring to FIGS. 1-3, a first embodiment of the present invention is illustrated as a liner (L) having a closed distal end and an open proximal end for receiving a residual limb of a below-the-knee BTK amputee. The liner (L) is comprised of an elastomeric material discussed in more detail hereinbelow. The liner (L) is configured to entirely cover the lower portion of the residual limb from the terminal end up to a point above the knee. As illustrated in FIGS. 1-3, the first embodiment of the liner (L) is covered over all of the anterior thereof, which includes the forward most point of the patella (1), with an overlay of a first material (2); and over all of the posterior thereof, which includes the popliteal fossa (3), with an overlay of a second material (4). As illustrated in FIG. 4, in a second embodiment, the liner (L) is covered over a portion of the anterior thereof from the open end to a point below the forward most point of the patella (1), with an overlay of a first material (2); and over a portion of the posterior thereof from the open end to a point below the popliteal fossa (3), with an overlay of a second material (4). As illustrated in FIG. 5, in a third embodiment, the liner (L) is covered over a portion of the anterior thereof from a point below the open end to a point below the forward most point of the patella (1), with an overlay of a first material (2); and over a portion of the posterior thereof from a point below the open end to a point below the popliteal fossa (3), with an overlay of a second material (4). As illustrated in FIG. 1, the edges of the anterior and posterior overlays are coupled to each other, directly or indirectly, on both sides of the knee, along the edges thereof that intersect a plane generally passing through the longitudinal extent of the residual limb generally midway between the anterior and posterior points such that first and second materials are elastically connected by a means (5) in addition to being attached to the underlying liner (L). The means (5) can be any conventional connection such as a strip of material attached along the edges of materials (2) and (4), or can be an overlap of one material edge adhered over the edge of the other as illustrated in FIG. 1A, or can be abutting edges sewn together with overlapping cross-stitches (6) as illustrated in FIG. 1B.

In the preferred embodiments of the present invention, the materials (2) and (4) have anisotropic properties. It is noted that a material with a greater Modulus of Elasticity (ME) is stiffer (i.e., not as easily stretched) than a material with a lower ME. The posterior portion of the elastomeric liner (L) is overlaid with a material (4) having a longitudinal and transverse modulus of elasticity (ME) greater than that of the elastomeric liner (L). The anterior portion of the elastomeric liner is overlaid with a material (2) having a longitudinal and transverse ME greater than the ME of the elastomeric liner (L). The longitudinal ME of the material (2) overlaying the anterior region is less than the longitudinal ME of the material (4) overlaying the posterior region. Thus, the material (2) is easier to stretch than the material (4).

In the preferred embodiments, the longitudinal elongation of anterior material (2) is in the range of from about 30% to about 180%. In more preferred embodiments, the longitudinal elongation of anterior material (2) is in the range of from about 50% to about 150%.

In preferred embodiments, the transverse elongation of anterior material (2) is in the range of from about 50% to about 250%. In more preferred embodiments, the transverse elongation of anterior material (2) is in the range of from about 75% to about 225%.

In preferred embodiments, the longitudinal elongation of posterior material (4) is in the range of from about 5% to about 75%. In more preferred embodiments, the longitudinal elongation of posterior material (4) is in the range of from about 5% to about 50%.

In preferred embodiments, the transverse elongation of posterior material (4) is in the range of from about 50% to about 250%. In more preferred embodiments, the transverse elongation of posterior material (4) is in the range of from about 75% to about 225%.

A main feature of the present invention is that the balance of the longitudinal and transverse elongations of the two overlaying materials (2) and (4) is effective in reducing or eliminating buckling.

With the above elongation ratios, when the liner is fully donned, the longitudinal and transverse elongations of the two overlaying materials will be set according to the size and circumferential dimensions of the residual limb of the patient. As the knee is flexed as illustrated in FIG. 3, the relatively relaxed liner surface disposed over the kneecap (the "anterior surface") must stretch and bend (arrows B) in order to accommodate the change in conformation of the knee joint, as well as the increase in anterior skin surface area which accompanies the change. Due to the transverse elongation of both materials (2) and (4) being equal and the increased anterior skin surface area when the knee is flexed, the anterior material (2) will cause the posterior material (4) to stretch in the transversely (arrow C). Furthermore, since the anterior material (2) stretches longitudinally when the knee is flexed, the anterior material (2) will contract transversely to a certain degree (arrow C), which will also contribute to the transverse_stretching of the posterior material (4). This transverse stretching of the posterior material (4) will, in turn, cause the posterior material (4) to contract longitudinally (arrows A) to a certain degree along with contraction thereof caused by flexing of the knee.

The liner (L) of the present invention comprises a layer of elastomeric material preferably of a type compatible with long periods of dynamic wearer contact. Such materials are known in the art and may include the following polymers, as well as gels which comprise them: polyurethanes; block copolymers such as styrene block copolymers, general non-limiting examples of which may include SEBS-, SEPS-, SEEPS-, SEEBS-, and other type styrene block copolymers. Further non-limiting examples of styrene block copolymers which may be useful in the liner of the present invention include so called "controlled distribution polymers," such as, for example, those disclosed in U.S. Pat. No. 7,226,484; United States Patent Application Publication No. 20070238835; and United States Patent Application Publication No. 20050008669. Other potentially useful polymers may include certain so-called "crystalline" polymers, such as, for example, polymers disclosed in U.S. Pat. Nos. 5,952,396; 6,420,475; and 6,148,830. The above list is non-limiting, and in general, the list of acceptable polymers and gels includes those known in the art to be useful for the fabrication of prosthetic liners. By the term "gel," is meant a polymer mixed with a plasticizer. A suitable liner is the "EZ Gel liner," available from Alps South L.L.C.

The lateral connections between anterior and posterior regions may comprise ties or other physical connections, such as regions of, elastic, elastomeric, or even non-elastic materials, which are attached to both anterior and posterior regions. One or both of said attachments may be edge-to-edge (adhered or stitched), bottom-to-top (for example, top of anterior/posterior region adhered to bottom of connecting region), or other. The connecting regions may be adhered to the elastomeric liner as well, if desired.

By "overlaying" the elastomeric liner with a layer of elastic fabric or other elastomeric material, it is meant that the material is adhered to the elastomeric liner over at least a portion of the contact surfaces. The method of adherence of the overlaying materials to the liner can be any number of well known techniques such as, molding, rolling, brushing, etc. the elastomeric liner directly to the material surface, or by applying an intermediate layer adhering the anterior and posterior materials to the elastomeric liner.

The materials chosen for the anterior and posterior surfaces have elasticity characteristics such that the materials can stretch in mutually perpendicular directions. For example fabrics having sufficient elasticity can be used. Examples of such fabrics are fabrics which are "crimped" into corrugated or contracted formations which allow the fabric to stretch when directionally stressed or pulled at an angle, particularly a right angle, to the corrugations. Such fabrics are often combinations of textile and elastomeric materials, where the elastomeric material is combined with the fabric in such a way that the fabric comprises gathered or corrugated sections which flatten out when pulled. Such fabrics can additionally or alternatively be comprised of fibers, woven or otherwise, that themselves contribute to the elasticity of the fabric. Other oriented elastic materials, such as those having directionally differential elasticity such as, for example, oriented gels (for example, styrene block copolymers or polymers which have been oriented during fabrication and/or heating by physical stress or other mechanisms, for example, oriented polymeric materials containing significant amounts of polyethylene) fabrics which have directionally differential elastic capabilities or elastomeric component. Preferred fabrics are knit fabrics made from stretchable yarns, which can have equal or different longitudinal or transverse elongations, as well as directional elasticities which are independent, or with some degree of dependence, as described above.

The above discussion is illustrative but not limiting with respect to the liner of the present invention. In general, liners with overlays as described herein exhibit reduced buckling (fewer folds, folds of lesser depth) or no buckling with respect to the liner in the absence of overlays. Preferably a reduction in buckling is observed at flexion angles in the range of from 0 to 30 degrees, and more preferably at flexion angles in the range of from 0 to 45 degrees.

Referring to FIG. 4, the second embodiment of the present invention is illustrated. FIG. 4 shows the inventive concept applied to an elastomeric sleeve (L) having anterior material (2) and posterior material (4) overlays do not extend to the stump end of the liner, and are laterally connected by a seam.

Referring to FIG. 5, the third embodiment of the present invention is illustrated. FIG. 5 shows the inventive concept applied to an elastomeric sleeve (L) having anterior material (2) and posterior material (4) overlays do not extend to the stump end or to the open end of the liner, and are laterally connected by a seam.

Figure 6:
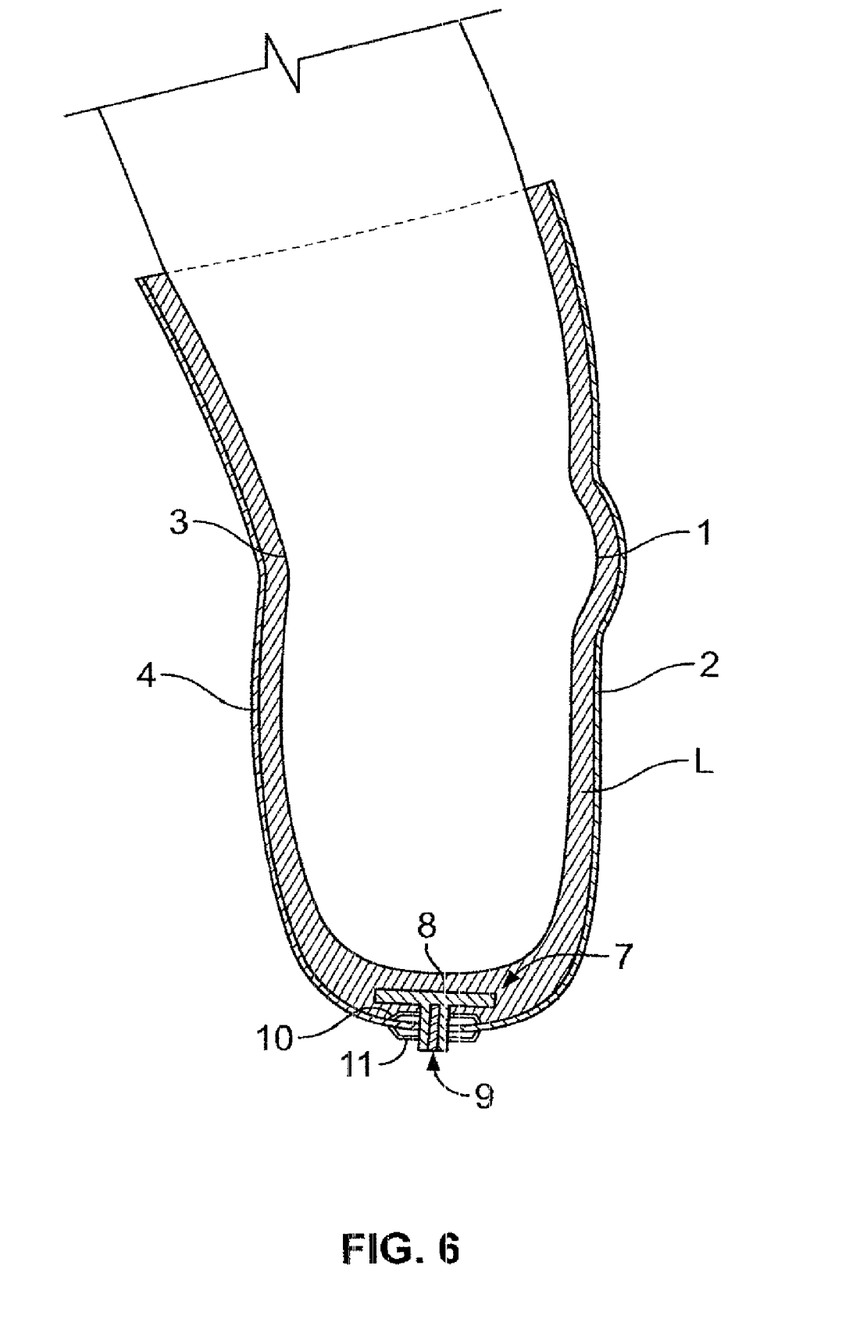
FIG. 6 illustrates another embodiment of the present invention in which the distal end of the liner is provided with an insert member embedded within the elastomeric liner for attaching the liner to a prosthetic socket.

Referring to FIG. 6, the fourth embodiment of the present invention is illustrated. FIG. 6 shows the inventive concept with the addition of an insert member (7) molded into the distal end of the liner. The insert member (7) is made of metal or plastic, preferably brass, and includes a generally disc-shaped base (8) and a hollow cylindrical stem (9) extending therefrom. Base (8) is drawn flat, but could also be an umbrella-like configuration so that it conforms to the curvature of the distal end of the liner. The hollow stem (9) is internally threaded and adapted to threadedly receive a connector member (not shown) for locking the liner to the interior of a prosthetic socket. As illustrated in FIG. 6, the base (8) and part of the stem (9) is embedded in the gel of the liner and part of the stem is not embedded in the gel. The insert member (7) also includes two grommets (10) and (11). These grommets are made of metal or plastic, preferably brass, and have a central aperture that is slightly smaller than the circumference of the stem (9). The grommets are fitted onto the stem either by force fit in which the grommets are wedged onto the stem, or the stem could include two annular grooves (not shown) into which the central aperture of each respective grommet will snap into once the grommets are applied to the stem. Alternatively, the grommets could be held in place by adhesive or any conventional welding technique. Further, as illustrated in FIG. 6, the distal ends of the anterior and posterior materials (2) and (4) are formed with a neck-receiving opening through which stem (9) extends. Thus, during the manufacturing process of the present invention, the grommet (10) is first fixed on the stem (9). The stem (9) is placed through the neck-receiving opening at the distal ends of the materials (2) and (4). The gel is then injected onto the materials within a molding machine in a conventional manner to form the liner. Once the liner is formed and removed from the molding machine, the grommet (11) is then fitted onto the stem (9). Thus, as the grommet (11) is forced further onto the stem (9), the materials surrounding the neck-receiving opening is then positioned and held between the jaws of the grommets (10) and (11). The grommet (11) is then fixed onto the stem (9) in one of the various manners discussed above.

Figure 7:
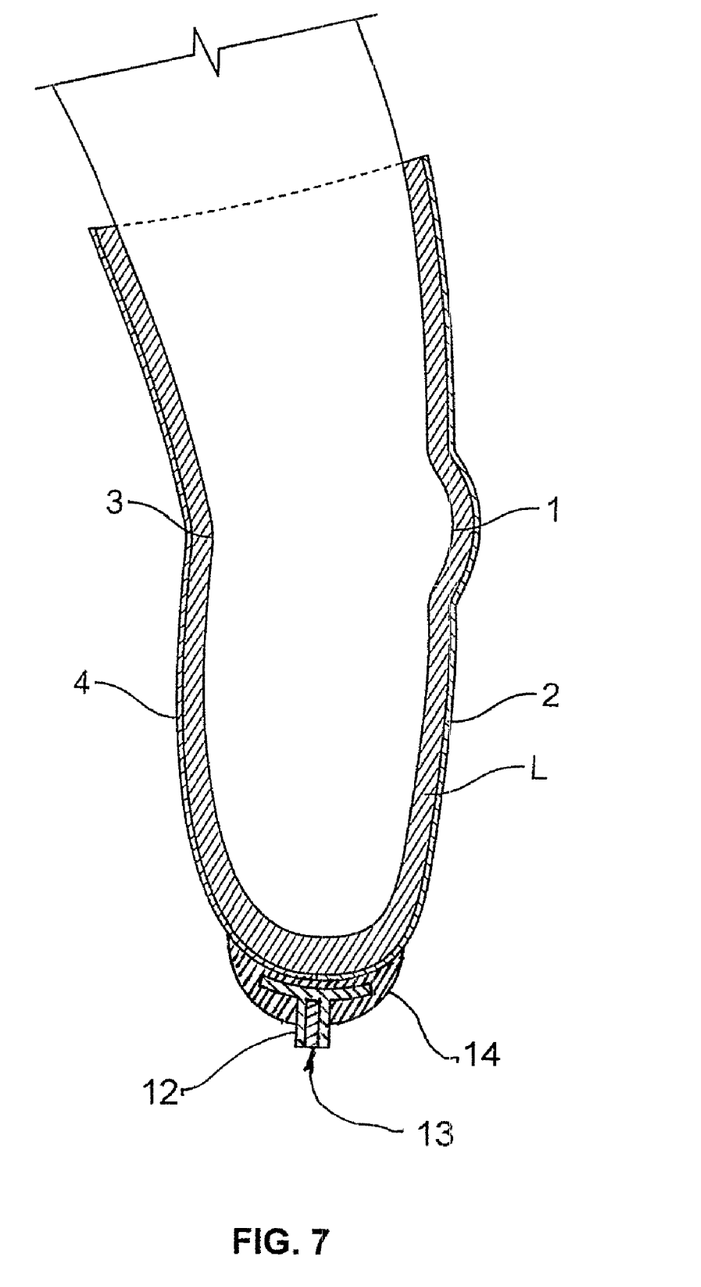
FIG. 7 illustrates another embodiment of the present invention in which the distal end of the liner is provided with an insert member either molded to or adhered to the fabric on the distal end of the liner for attaching the liner to a prosthetic socket.
Figure 8:
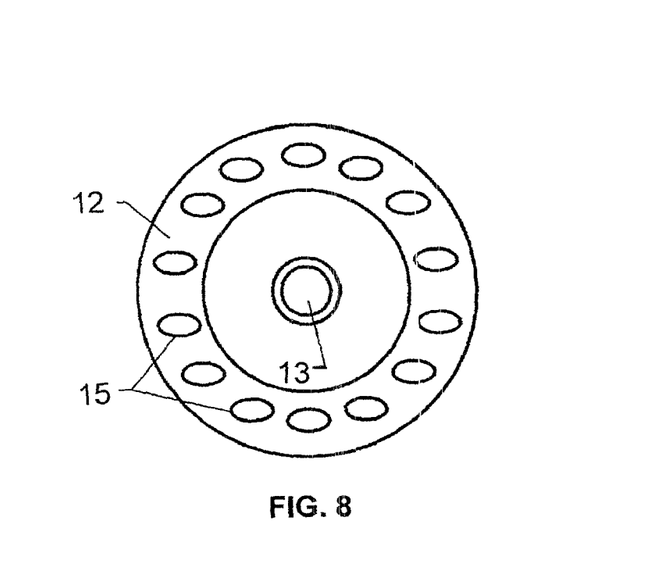
FIG. 8 illustrates a front view of the insert member that is used in the embodiments of FIGS. 6 and 7.

Referring to FIG. 7, the fifth embodiment of the present invention is illustrated. FIG. 7 shows the inventive concept with the addition of an insert member (12) molded or adhered onto the fabric on the distal end of the liner with a polymeric material (14) which can be any well polymeric material such as those discussed hereinabove. The base (12) is made of metal or plastic, preferably brass, and includes an umbrella-shaped base and a hollow cylindrical stem extending therefrom. Base (12) has an umbrella-like configuration so that it conforms to the curvature of the distal end of the liner. The hollow stem is internally threaded and adapted to threadedly receive a connector member (not shown) for locking the liner to the interior of a prosthetic socket. As illustrated in FIG. 8, the umbrella-shaped base includes a series of holes 15 through which the polymeric material flows during the process of molding the insert member onto the liner. The process of molding the insert member to the liner can be of any well known conventional technique.

We claim:

1. A locking liner comprising:

an elastomeric liner having a closed distal end and an open proximal end for donning over a residual limb of a below-the-knee amputee, said liner sized and configured to surround a residual limb of a patient and extend above and below said knee joint;

said liner having an elastomeric inner layer defining an inner surface for facing the limb of the patient and an outer surface; said outer surface defining an anterior region and a posterior region; said regions being demarcated by an imaginary plane extending substantially midway between the front most portion and rear most portion of the limb along the length of the limb when said liner is worn;

said anterior region of said outer surface having an elastomeric anterior single unitary piece of material secured thereto; said posterior region of said outer surface having an elastomeric posterior single unitary piece of material secured thereto;

said anterior piece of material being coextensive with said posterior piece of material;

said anterior and posterior materials having edge portions extending along said imaginary plane and secured together, wherein said edge portions are secured together along substantially their entire lengths;

said anterior and posterior materials having predetermined transverse elongation;

said anterior material having a longitudinal elongation in the range of from about 30% to about 180%;

said posterior material having a longitudinal elongation in the range of from about 5% to about 75%;

said elastomeric inner layer having greater transverse and longitudinal elongations than said anterior and posterior materials;

an insert member molded or adhered onto the anterior and posterior materials over the distal end of said liner and adapted to receive a connector for locking said liner into a prosthetic socket when worn on a residual limb of a patient; and said anterior and posterior materials each having a longitudinal elongation selected from said range of longitudinal elongations and each having said predetermined transverse elongation such that when said liner is donned onto a limb of a patient over the knee and the limb is flexed about the knee, the anterior material over the knee stretches longitudinally and contracts transversely causing the posterior material behind the knee to stretch transversely which, in turn, causes the posterior material to contract longitudinally thereby buckling of the liner behind the knee is substantially reduced or eliminated.

2. A prosthesis as claimed in claim 1, wherein said anterior and posterior materials both have a transverse elongation in the range of from about 50% to about 250%.

3. A prosthesis as claimed in claim 2, wherein said anterior and posterior materials both have a transverse elongation in the range of from about 75% to about 225%.

4. A prosthesis as claimed in claim 3, wherein said anterior material having a longitudinal elongation in the range of from about 50% to about 150%.

5. A prosthesis as claimed in claim 4, wherein said posterior material having a longitudinal elongation in the range of from about 5% to about 50%.

6. A prosthesis as claimed in claim 3, wherein said posterior material having a longitudinal elongation in the range of from about 5% to about 50%.

7. A prosthesis as claimed in claim 2, wherein said anterior material having a longitudinal elongation in the range of from about 50% to about 150%.

8. A prosthesis as claimed in claim 7, wherein said posterior material having a longitudinal elongation in the range of from about 5% to about 50%.

9. A prosthesis as claimed in claim 2, wherein said posterior material having a longitudinal elongation in the range of from about 5% to about 50%.

10. A prosthesis as claimed in claim 1, wherein said anterior and posterior materials both have a transverse elongation in the range of from about 75% to about 225%.

11. A prosthesis as claimed in claim 10, wherein said anterior material having a longitudinal elongation in the range of from about 50% to about 150%.

12. A prosthesis as claimed in claim 11, wherein said posterior material having a longitudinal elongation in the range of from about 5% to about 50%.

13. A prosthesis as claimed in claim 10, wherein said posterior material having a longitudinal elongation in the range of from about 5% to about 50%.

14. A prosthesis as claimed in claim 1, wherein said anterior material having a longitudinal elongation in the range of from about 50% to about 150%.

15. A prosthesis as claimed in claim 14, wherein said posterior material having a longitudinal elongation in the range of from about 5% to about 50%.

16. A prosthesis as claimed in claim 1, wherein said posterior material having a longitudinal elongation in the range of from about 5% to about 50%.

17. A prosthesis as claimed in claim 1, wherein said edge portions are secured together by adhering overlapping edges, cross-stitching abutting edges, or sewing a strip of material across abutting edges.

18. A prosthesis as claimed in claim 1, wherein said anterior and posterior materials extend over said closed distal end of said liner over which said insert member is attached.

19. A prosthesis as claimed in any one of claims 1-18, wherein said insert member comprises a base and a centrally located hollow tubular stem extending from said base, said base and a first portion of said stem being encased in polymeric material either molded or adhered onto the distal end of said liner, said stem having a second portion extending from said polymeric material.

20. A prosthesis as claimed in claim 19, wherein said base comprises an umbrella-shaped disc having a series of holes through which said polymeric material flows during the molding process.

21. A prosthesis as claimed in claim 20, wherein said hollow tubular stem comprises internal threads for threadedly receive a connector member (not shown) for locking the liner to the interior of a prosthetic socket.

* * * * *